(12) United States Patent
Riermeier et al.

(10) Patent No.: US 6,884,887 B1
(45) Date of Patent: Apr. 26, 2005

(54) METHOD FOR PRODUCING AMINES BY HOMOGENEOUSLY CATALYZED REDUCTIVE AMINATION OF CARBONYL COMPOUNDS

(75) Inventors: Thomas Riermeier, Floersheim (DE); Karl-Josef Haack, Niedernhausen (DE); Uwe Dingerdissen, Seeheim-Jugenheim (DE); Armin Boerner, Rostock (DE); Vitali Tararov, Moskau (RU); Renat Kadyrov, Rostock (DE)

(73) Assignee: Degussa AG, Duesseldorf (DE)

( * ) Notice: Subject to any disclaimer, the term of this patent is extended or adjusted under 35 U.S.C. 154(b) by 31 days.

(21) Appl. No.: 10/030,946
(22) PCT Filed: Jun. 29, 2000
(86) PCT No.: PCT/EP00/06056
§ 371 (c)(1),
(2), (4) Date: Mar. 26, 2002
(87) PCT Pub. No.: WO01/05741
PCT Pub. Date: Jan. 25, 2001

(30) Foreign Application Priority Data

Jul. 17, 1999 (DE) .......................................... 199 33 611

(51) Int. Cl.$^7$ ........................................... C07D 265/30
(52) U.S. Cl. ....................... 544/106; 558/303; 564/305; 564/446
(58) Field of Search ................................ 564/305, 446; 558/303; 544/106

(56) References Cited

U.S. PATENT DOCUMENTS 2,879,293 A 3/1959 Goldberg et al.

FOREIGN PATENT DOCUMENTS

EP 0 893 430 1/1999
JP 11 343269 12/1999

OTHER PUBLICATIONS

L. Marko et al.: "Homogeneous Reductive Amination with Cobalt and Rhodium Carbonyis as Catalysts" Journal of Organometallic Chemistry, vol. 81, pp. 411–414.

*Primary Examiner*—Kamal Saeed
(74) *Attorney, Agent, or Firm*—Oblon, Spivak, McClelland, Maier & Neustadt, P.C.

(57) ABSTRACT

The invention relates to the preparation of chiral or achiral amines by reaction of aldehydes or ketones with ammonia or primary or secondary amines in the presence of hydrogen and in the presence of homogeneous metal catalysts under mild conditions. Metal catalysts which can be used are complexes of late transition metals with chiral or achiral phosphorus-containing ligands.

21 Claims, No Drawings

METHOD FOR PRODUCING AMINES BY HOMOGENEOUSLY CATALYZED REDUCTIVE AMINATION OF CARBONYL COMPOUNDS

DESCRIPTION

The invention relates to the preparation of amines by reaction of aldehydes or ketones with ammonia or primary or secondary amines in the presence of hydrogen and in the presence of homogeneous metal catalysts under mild conditions. Metal catalysts which can be used are complexes of late transition metals with phosphorus-containing ligands. The process of the invention also makes possible the synthesis of enantiomerically pure or enantiomerically enriched amines by means of an enantioselective or diastereoselective reaction.

Racemic and enantiomerically pure amines play a dominant role in numerous complex natural substances, for example alkaloids, vitamins or amino acids, whose chemical, pharmaceutical and industrial importance is undisputed. As chemical intermediates amines are employed in, for example, the synthesis of pharmaceuticals, agrochemicals, food additives, dyes or cosmetics. In the field of active compounds, amino acids and amino alcohols play a predominant role.

Heterogeneously catalyzed amination of ketones and aldehydes plays an important role in the synthesis of unfunctionalized and functionalized amines (Catalytic Hydrogenation over Platinum Metals, Academic Press, New York, 1967, p. 291 ff; Catalytic Hydrogenation in Organic Synthesis, Academic Press, New York, 1979, 165 ff). Heterogeneous catalysts which have been used are, for example, $CuCr_2O_4 \cdot CuO$ (Kurc et al., Chem. Prum. 1987, 37, 26), Re or Cu (DE-A-19631521), Raney nickel (EP-A0011401), Ru supported on $MgO/Al_2O_3$ (DE-A-4010252), Ru supported on $\gamma$—$Al_2O_3$ (EP-A-0449089), Cu supported on $Al_2O_3$ (Barrault et al., Rev. Fr. Corps Gras 1991, 38, 103) or Fe (CA-A-0907059).

However, a heterogeneous reaction has, in principle, considerable disadvantages (J. Hagen, Technische Katalyse, VCH, Weinheim, 1996, p. 10). It has been found that characteristic problems occur in the mass transfer between the phases and result in an appreciable reduction in the reaction rate. For this reason, high reaction temperatures of up to 150° C. and pressures of up to 250 bar are usually necessary for the heterogeneously catalyzed amination. This represents a considerable economic disadvantage in the construction and operation of such plants. The development of new catalysts which make it possible to carry out the desired reaction under milder conditions is therefore of exceptional interest. Furthermore, tolerance of further functional groups which are usually present in the molecule, e.g. in the synthesis of active compounds, is significantly restricted because of the drastic reaction conditions. In addition, the heterogeneous catalysts can be characterized only with difficulty, a fact which can seriously impair the reproducibility of the catalysis results and make rational catalyst design or modification to meet specific objectives difficult or even impossible.

Only very few examples of catalysts in homogeneous systems are known in the literature: dimethylglyoximate complexes of cobalt and rhodium (M. V. Klyuev, M. L. Khidekel, Transition Met. Chem., 1980, 5 134–139). To activate the catalysts, almost stoichiometric amounts of sodium borohydride have to be used. Furthermore, Rh and Co carbonyl complexes (L. Marko, J. Bakos Journal of Organometallic Chemistry, 1974, 81, 411–414) and cobalt-cyano-complexes (M. Murakami, J.-W. Kang Bull. Chem. Soc. Japan, 1963, 36, 763–768) have been described. However, owing to the large amounts of catalyst and the drastic conditions required, the processes described are not practical.

JP 11-343269 describes the synthesis of octylamine from octanal and ammonia, in which a series of homogeneous catalysts such as iron(II) sulfide, nickel acetylacetonate, carbonylrhodium acetylacetonate, palladium acetylacetonate, dodecacarbonylosmium(III), hexacarbonylindium(VI), 1,5-cyclooctadieneplatinum dichloride and ruthenium acetylacetonate with 2,2'-bipyridyl in an extremely complicated process at a high temperature of 150° C. The hydroaminomethylation reaction (P. Eilbracht et al. Chem. Rev. 1999, 99, 3329–3364), for which a reductive amination of an intermediate has been postulated but not proven to date, also proceeds under drastic reaction conditions.

It is therefore an object of the present invention to find a process by means of which the amination can be carried out under mild conditions and the abovementioned problems can be avoided.

Furthermore, the process should also allow the synthesis of enantiomerically pure or enantiomerically enriched amines by use of chirally modified catalysts.

It has now surprisingly been found that the desired amines can be obtained very efficiently by the reductive amination of ketones and aldehydes in the presence of catalytically active transition metal complexes based on phosphorus-containing ligands under very mild conditions.

Under these mild reaction conditions, an enantioselective reaction is possible when using chiral ligands.

The transition metal catalysts used give good to very good yields of the desired amine in the reductive amination. At the same time, a very high amine/alcohol ratio in the products can be achieved.

The process of the invention overcomes the known disadvantages of the metal-catalyzed reductive aminations described hitherto.

The present invention accordingly provides a process for preparing amines of the formula (III)

by reacting a compound of the formula (I)

with a compound of the formula (II)

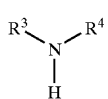

where the radicals $R^1$ to $R^4$ are selected independently from the group consisting of hydrogen, $(C_1-C_{24})$-alkyl, $(C_2-C_{24})$-alkenyl, $(C_2-C_{24})$-alkynyl, $(C_6-C_{10})$-aryl, $CF_3$, CN, COOH, COOM, where M is a cation, CHO, $SO_3H$, COO-alkyl-$(C_1-C_8)$, $CONH_2$, CONHalkyl-$(C_1-C_8)$, CONalkyl$_2$-$(C_1-C_8)$, CO-alkyl-$(C_1-C_8)$, CO-phenyl, COO-phenyl, COO-aryl-$(C_6-C_{10})$, CO-aryl-$(C_6-C_{10})$, P(aryl)$_2$, Palkyl$_2$—$(C_1-C_8)$, PO(aryl)$_2$, POalkyl$_2$-$(C_1-C_4)$, $PO_3H_2$, POalkyl-$(C_1-C_4)$(O-alkyl-$(C_1-C_6)$), PO(O-alkyl-$(C_1-C_6)$)$_2$, $SO_3$-alkyl-$(C_1-C_4)$, $SO_2$-alkyl-$(C_1-C_6)$, SO-alkyl-$(C_1-C_6)$ or Si(alkyl)$_3$—$(C_1-C_8)$, and/or $R^3$ and $R^4$ are selected independently from the group consisting of O-alkyl-$(C_1-C_8)$, OCO-alkyl-$(C_1-C_8)$, O-aryl, fluorine, OH, $NH_2$, NH-alkyl-$(C_1-C_8)$, N-alkyl$_2$-$(C_1-C_8)$, NHCO-alkyl-$(C_1-C_4)$, NHaryl-$(C_6-C_{10})$, NHCOO-alkyl-$(C_{1-4})$, where alkyl is, for the purposes of the present invention, an unbranched or branched aliphatic or cyclic or heterocyclic radical containing at least one (1–4) nitrogen, sulfur or oxygen atom, alkenyl is an olefinic hydrocarbon, alkynyl is an acetylenic hydrocarbon and aryl is an aromatic radical which may also be an aromatic containing at least one (1–4) nitrogen, sulfur or oxygen atom. Alkyl, alkenyl, alkynyl and also aryl may bear substituents selected independently from among hydrogen, O-alkyl-$(C_1-C_8)$, OCO-alkyl-$(C_1-C_8)$, O-phenyl, phenyl, aryl$(C_6-C_{10})$, fluorine, chlorine, bromine, iodine, OH, $NO_2$, $CF_3$, CN, COOH, COOM, where M is a cation (Li$^+$, Na$^+$, K$^+$, Mg$^{2+}$, Ca$^{2+}$, $NH_4^+$, $N(C_1-C_{10}$-alkyl)$_4^+$, $N(C_1-C_{10}$alkyl/$C_6-C_{10}$-aryl)$_4^+$), CHO, $SO_3H$, $NH_2$, NH-alkyl-$(C_1-C_8)$, N-alkyl$_2$-$(C_1-C_8)$, NHCO-alkyl-$(C_1-C_4)$, COO-alkyl-$(C_1-C_8)$, $CONH_2$, CO-alkyl-$(C_1-C_8)$, NHCOH, NHCOO-alkyl-$(C_1-C_4)$, CO-phenyl, COO-phenyl, COO-aryl-$(C_6-C_{10})$, CO-aryl-$(C_6-C_{10})$, CHCH—$CO_2$-alkyl-$(C_1-C_8)$, P(aryl)$_2$, $CHCHCO_2H$, P-alkyl$_2$-$(C_1-C_8)$, PO-aryl$_2$, POalkyl$_2$-$(C_1-C_4)$, $PO_3H_2$, POalkyl-$(C_1-C_4)$(O-alkyl-$(C_1-C_6)$), PO(O-alkyl-$(C_1-C_6)$)$_2$, $SO_3$-alkyl-$(C_1-C_4)$, $SO_2$-alkyl-$(C_1-C_6)$, SO-alkyl-$(C_1-C_6)$ or Si(alkyl)$_3$—$(C_1-C_8)$.

Both $R^1$ and $R^2$ and also $R^3$ and $R^4$ can be linked by covalent bonds so that $R^1$ and $R^2$ and/or $R^3$ and $R^4$ in each case form a four- to eight-membered ring. $R^1$ or $R^2$ may also be part of an organometallic compound.

The reaction is carried out in the presence of hydrogen and a homogeneous catalyst system comprising at least one metal atom selected from the group consisting of Rh, Ru, Ir, Pd, Pt, Co and Ni and one or more monodentate or bidentate achiral or chiral ligands of the formula (IV) or (V)

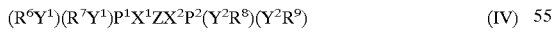

where $R^6$ to $R^9$ are identical or different and are a hydrogen atom or a $C_1-C_{50}$ group, e.g. $C_1-C_{24}$-alkyl, $C_2-C_{20}$-alkenyl, $C_3-C_8$-cycloalkyl, $C_5-C_8$-cycloalkenyl, $C_6-C_{14}$-aryl, phenyl, naphthyl, fuorenyl, $C_2-C_{13}$-heteroaryl, where the number of heteroatoms from the groups consisting of N, O, S can be 1–4, where the cyclic aliphatic or aromatic radicals are preferably 5- to 7-membered rings, and in which all the abovementioned substituents may each be substituted by one or more substituents selected independently from among hydrogen, $C_1-C_{20}$-alkyl, $C_2-C_{20}$-alkenyl, $C_1-C_{10}$-haloalkyl, $C_3-C_8$-cycloalkyl, $C_5-C_8$-cycloalkenyl, $C_2-C_9$-heterocycloalkyl, $C_1-C_9$-heterocyclo-alkenyl, $C_6-C_{14}$-aryl, phenyl, $C_2-C_{13}$-heteroaryl, where the number of heteroatoms from the group consisting of N, O, S can be 1–4, $C_1-C_{10}$-alkoxy, OCO-alkyl-$(C_1-C_8)$, O-aryl-$(C_5-C_{10})$, O-phenyl, $C_1-C_9$trihalomethylalkyl, fluoro, chloro, bromo, iodo, nitro, hydroxy, trifluoromethylsulfonato, oxo, thio, thiolato, amino, $C_1-C_8$-substituted amino of the types mono- and di-$C_1-C_8$-alkylamino or $C_2-C_8$-alkenylamino or mono-, di-, tri-$C_6-C_8$-arylamino or $C_1-C_8$-alkyl-$C_6-C_{10}$-arylamino, NH—CO-alkyl-$C_1-C_8$, NH—CO-aryl-$C_6-C_8$, cyano, $C_1-C_8$-acyloxy, carboxyl, carboxylato of the formula $COOR^{12}$, sulfinato, sulfonato of the formula $SO_3R^{12}$, phosphonato of the formula $PO_3H_2$, $PO_3HR^{12}$, $PO_3R^{12}{}_2$, where $R^{12}$ is either a monovalent cation, $NH_4^+$, $N(C_1-C_{10}$-alkyl)$_4^+$, $N(C_1-C_{10}$-alkyl/$C_6-C_{10}$-aryl)$_4^+$, $C_1-C_{18}$-alkyl or $C_6$-aryl, tri-$C_1-C_6$-alkylsilyl, and where two of these substituents may also be bridged, and $R^6$ and $R^7$ and/or $R^8$ and $R^9$ may also be linked by a covalent bond so as to form a cyclic compound having from four to eight atoms, $X^1$ and $X^2$ are each, independently of one another, a direct phosphorus-carbon bond, O, S or $NR^{10}$, where $R^{10}$ corresponds to one of the radicals defined for $R^6-R^9$, $Y^1$ and $Y^2$ is a direct phosphorus-carbon bond, —O— or —$NR^{11}$—, where $R^{11}$ corresponds to one of the radicals defined for $R^6-R^9$, Z corresponds to 1–6 carbon atoms which are bound to one another by single or multiple bonds and connect the unit $(R^6Y^1)(R^7Y^1)PX^1$ to the unit $X^2P(Y^2R^8)(Y^2R^9)$, where Z may be part of an aliphatic, cycloaliphatic, olefinic, cycloolefinic system which may contain from one to four heteroatoms from the group consisting of N, O, S, a metallocene, in particular a ferrocene, a 1,1'-disubstituted ferrocene, 1-(1-ethylenyl)-2-ferrocenyl or a 1,2-disubstituted ferrocene, or one or more aromatic or heteroaromatic ring systems, where the ring system comprises a total of from 2 to 14 carbon atoms which may be monosubstituted or polysubstituted by substituents as specified for $R^6-R^9$ or directly by $C_1-C_{10}$-alkoxy, OCO-alkyl-$(C_1-C_8)$, O-aryl-$(C_5-C_{10})$, O-phenyl, $C_1-C_9$-trihalomethylalkyl, trifluoromethyl, trichloromethyl, fluoro, chloro, bromo, iodo, nitro, hydroxy, trifluoromethylsulfonato, oxo, thio, thiolato, amino, $C_1-C_8$-substituted amino of the formulae $NH_2$, NH-alkyl-$C_1-C_8$, NH-aryl-$C_5-C_6$, N-alkyl$_2$—$C_1-C_8$, N-aryl$_2$-$C_5-C_6$, N-alkyl$_3$—$C_1-C_8^+$, N-aryl$_2$—$C_5-C_6$-aryl-$C_5-C_6^+$, $C_1-C_6$-acyloxy, carboxylato of the formulae COOH and $COOR^{12}$, sulfinato, sulfonato of the formulae $SO_3H$ and $SO_3R^{12}$, phosphonato of the formulae $PO_3H_2$, $PO_3HR^{12}$ and $PO_3R^{12}{}_2$, where $R^{12}$ is either a monovalent cation, $NH_4^+$, $N(C_1-C_{10}$-alkyl)$_4^+$, $N(C_1-C_{10}$-alkyl/$C_6-C_{10}$-aryl)$_4^+$, $C_1-C_8$-alkyl or $C_6$-aryl, $C_1-C_6$-trialkylsilyl, NHCO-alkyl-$(C_1-C_4)$, COO-alkyl-$(C_1-C_8)$, $CONH_2$, CON(alkyl-$(C_1-C_8)$)$_2$, CO-alkyl-$(C_1-C_8)$, CO-alkenyl-$(C_1-C_8)$, NHCOO-alkyl-$(C_1-C_4)$, CO-aryl-$(C_6-C_{10})$, CO-phenyl, COO-aryl-$(C_6-C_{10})$, COO-phenyl, CHCH—$CO_2$-alkyl-$(C_1-C_8)$, $CHCHCO_2H$, and P is a trivalent phosphorus atom.

In a preferred embodiment, $R^1$ to $R^4$ are each, independently of one another, hydrogen, $(C_1-C_{12})$-alkyl, $(C_2-C_{12})$-alkenyl, $(C_2-C_{12})$-alkynyl, $(C_6-C_{10})$-aryl, $CF_3$, CN, COOH, COOM, where M is a cation (Li$^+$, Na$^+$, K$^+$, Mg$^{2+}$, Ca$^{2+}$, $NH_4^+$, $N(C_1-C_{10}$-alkyl)$_4^+$, $N(C_1-C_{10}$-alkyl/$C_6-C_{10}$-aryl)$_4^+$), COO-alkyl-($C_1$–$C_8$), $CONH_2$, CO-alkyl-($C_1$–$C_8$), CO-phenyl, COO-phenyl, COO-aryl-($C_6$–$C_{10}$), CO-aryl-($C_6$–$C_{10}$), PO(aryl-$C_6$–$C_{10}$)$_2$, POalkyl$_2$-($C_1$–$C_4$), $PO_3H_2$, PO(alkyl-($C_1$–$C_4$))(O-alkyl-($C_1$–$C_4$)), PO(O-alkyl-($C_1$–$C_6$))$_2$ or Si(alkyl)$_3$-($C_1$–$C_8$) and/or $R^3$ and $R^4$ are selected independently from the group consisting of O-alkyl-($C_1$–$C_8$), OCO-alkyl-($C_1$–$C_8$), O-aryl($C_6$–$C_{10}$), OH, $NH_2$, NH-alkyl-($C_1$–$C_8$), N-alkyl$_2$-($C_1$–$C_8$), NHCO-alkyl-($C_1$–$C_4$), NHCOO-alkyl-($C_1$–$C_4$), where alkyl is an unbranched or branched aliphatic or cyclic or heterocyclic (containing at least one nitrogen or oxygen atoms (1–4)) radical, alkenyl is an olefinic hydrocarbon, alkynyl is an acetylenic hydrocarbon and aryl is an aromatic radical which may also be an aromatic containing at least (1–4) one nitrogen, oxygen and/or sulfur atom. Alkyl, alkenyl and alkynyl and also aryl may bear substituents selected independently from among hydrogen, O-alkyl-($C_1$–$C_8$), OCO-alkyl-($C_1$–$C_8$), O-phenyl, phenyl, aryl-$C_6$–$C_{10}$, fluorine, chlorine, bromine, iodine, OH, $NO_2$, Si-alkyl$_3$-($C_1$–$C_8$), $CF_3$, CN, COOH, COOM, where M is a monovalent cation selected from the group consisting of Na, K, Rb, Cs, $NH_4$, N($C_1$–$C_{10}$-alkyl)$_4$, N($C_1$–$C_{10}$-alky/$C_6$–$C_{10}$-aryl)$_4$, and $SO_3H$, N-alkyl$_2$-($C_1$–$C_8$), $SO_2$-alkyl-($C_1$–$C_6$), SO-alkyl-($C_1$–$C_6$), NHCO-alkyl-($C_1$–$C_4$), COO-alkyl-($C_1$–$C_8$), $CONH_2$, CO-alkyl-($C_1$–$C_8$), CO-phenyl, COO-phenyl, COO-aryl-($C_6$–$C_{10}$), CO-aryl-($C_6$–$C_{10}$), PO-phenyl$_2$, POalkyl$_2$-($C_1$–$C_4$), $PO_3H_2$, POalkyl-($C_1$–$C_4$)(O-alkyl-($C_1$–$C_6$)), PO(O-alkyl-($C_1$–$C_6$))$_2$, Si(alkyl)$_3$—($C_1$–$C_8$), where alkyl and aryl are as defined above.

Both $R^1$ and/or $R^2$ and also $R^3$ and $R^4$ may be linked by covalent bonds so as to form a five- to seven-membered ring. $R^1$ or $R^2$ may also be part of an organometallic compound, in particular part of a ferrocene-containing molecule.

As homogeneous metal atom-ligand complex, preference is given to using metal complexes having central atoms from the group consisting of Rh, Ru, Ir, Pd, Pt, Ni, in particular those which contain rhodium or iridium as central atom.

Preferred ligands are ligands of the formula (IV), among which further preference is given to those in which $R^6$ to $R^9$ are each, independently of one another, $C_1$–$C_8$-alkyl, $C_5$–$C_6$-cycloalkyl, $C_6$-aryl, $C_4$–$C_5$-heteroaryl, where the number of heteroatoms is 1–2, selected from the group consisting of N, O, S, and the ring size is 5–6, or are naphthyl, with these groups being able to bear one or more substituents, preferably substituents selected independently from among hydrogen, $C_1$–$C_{10}$-alkyl, $C_1$–$C_6$-haloalkyl, $C_5$–$C_6$-cycloalkyl, $C_2$–$C_9$-heterocycloalkyl, $C_6$-aryl, phenyl, $C_4$–$C_5$-heteroaryl, where the number of heteroatoms from the group consisting of N, O, S, can be 1–2, $C_1$–$C_6$-alkoxy, OCO-alkyl-($C_1$–$C_6$), O-aryl-$C_6$, $C_1$–$C_6$-trihalomethylalkyl, fluoro, chloro, bromo, iodo, nitro, hydroxy, oxo, thio, thiolato, amino, $C_1$–$C_8$-substituted amino of the types mono-, di-, tri-$C_1$–$C_8$-alkylamino or $C_2$–$C_8$-alkenylamino or mono- and di-$C_6$–$C_8$-arylamino or $C_1$–$C_8$-alkyl-$C_6$–$C_8$-arylamino, NH—CO-alkyl-$C_1$–$C_8$, NHCO-aryl-$C_6$–$C_8$, $C_1$–$C_8$-acyloxy, carboxyl, carboxylato of the formula $COOR^{12}$, sulfinato, sulfonato of the formula $SO_3R^{12}$, phosphonato of the formula $PO_3H_2$, $PO_3HR^{12}$, $PO_3R^{12}{}_2$, where $R^{12}$ can be either a monovalent or divalent cation ($Li^+$, $Na^+$, $K^+$, $Mg^{2+}$, $Ca^{2+}$), $NH_4{}^+$, N($C_1$–$C_{10}$-alkyl)$_4{}^+$, N($C_1$–$C_{10}$-alkyl/$C_6$–$C_{10}$-aryl)$_4{}^+$, $C_1$–$C_8$-alkyl or $C_6$-aryl, and tri-$C_1$–$C_6$-alkylsilyl.

Preference is also given to ligands in which $Y^1$ and $y^2$ are each a direct phosphorus-carbon bond and in which Z comprises from one to four carbon atoms, particularly preferably two carbon atoms.

Particular preference is given to systems in which a seven-membered ring can be formed from Z, $X^1$, $X^2$, $P^1$ and $P^2$ together with a coordinated metal.

Z is preferably a $C_1$–$C_6$-alkyl or $C_2$–$C_6$-alkenyl group or is part of a $C_3$–$C_8$-cycloalkyl, $C_5$–$C_8$-cycloalkenyl, $C_2$–$C_9$-heterocycloalkyl, $C_1$–$C_9$-heterocycloalkyl, $C_6$–$C_{14}$-aryl, phenyl, naphthyl, fluorenyl, $C_2$–$C_9$-heteroaryl group, where the number of heteroatoms from the group consisting of N, O, S can be 1–4, where all these groups may be monosubstituted or polysubstituted as described above.

If Z is part of a cyclic structural element, three- to nine-membered ring systems are preferred. Particular preference is given to five- to seven-membered ring systems. The ring system may contain from one to four heteroatoms from the group consisting of N, O, S, preferably one or two. The nitrogen of the ring system can be present as $NR^{10}$, $NR^{10}R^{11+}$, $NR^{10}H^+$, $NC(O)R^{10}$. The ring systems can be monosubstituted or polysubstituted as indicated for $R^6$ to $R^9$ or directly by alkoxy, halo, nitro, hydroxy, oxo, thio, thiolato, amino, substituted amino, cyano, sulfonato, phosphonato, trialkylsilyl groups, where the substituents may also be bridged to one another.

Particularly preferred ring systems are phenyl, ferrocenyl, cyclopentyl, cyclohexyl, pyridyl, pyrrole, furyl, thiophene, tetrahydrofuran, tetrahydrothiophene, piperidyl, pyrrolidinyl, dioxolane or sulfolane rings which may each be unsubstituted or substituted as described above.

For the purposes of the present invention, metallocenes such as ferrocenes are formally included in the group of aromatics.

The ligand system used according to the invention preferably comprises, in $R^6$–$R^{12}$, independently of one another, alkyl, cycloalkyl or/and aryl which each contain from 1 to 20, in particular from 1 to 6, carbon atoms.

Examples of achiral or chiral ligands are compounds of the formulae VI, VII, VIII, IX, X and XI,

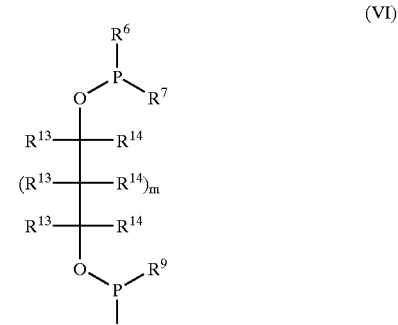

(VI)

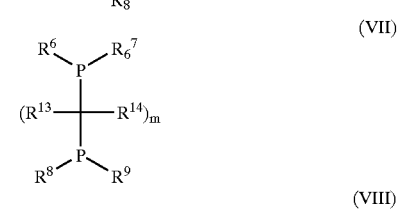

(VII)

(VIII)

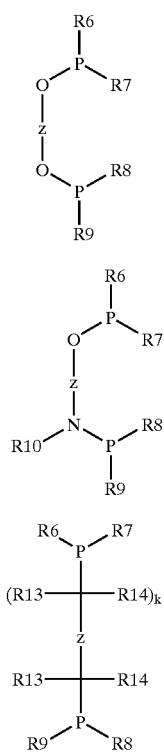

(IX)

(X)

(XI)

where $R^6$ to $R^{10}$ and $R^{13}$, $R^{14}$ are each, independently of one another, hydrogen, $(C_1-C_{24})$-alkyl, $(C_6-C_{10})$-aryl, O—$(C_1-C_{24})$-alkyl or O—$(C_6-C_{10})$-aryl and $R^6$ and $R^7$ and/or $R^8$ and $R^9$ may also be linked by a covalent bond so as to form a cyclic compound having from four to eight atoms, and m is 0, 1 or 2, n is 1, 2, 3, 4, 5 or 6 and k is 0 or 1.

Z is as defined above.

For the purposes of the present invention, alkyl is an unbranched or branched aliphatic or cyclic hydrocarbon and aryl is an aromatic radical which may also be an aromatic containing at least one nitrogen or oxygen atom.

Ligands of the formulae (VI) to (XI) include, for example, ones in which $R^6$ to $R^9$ and $R^{13}$, $R^{14}$ are selected independently from the group consisting of $(C_3-C_8)$-alkyl, $(C_6-C_{10})$-aryl, O—$(C_5-C_8)$-alkyl, O—$(C_6-C_{10})$-aryl, where alkyl is an unbranched or branched aliphatic or cyclic hydrocarbon and aryl is an aromatic radical, and m is from zero to two and n is from one to six. Both alkyl and aryl may bear substituents selected independently from among hydrogen, O-alkyl-$(C_1-C_8)$, O-phenyl, phenyl, aryl, fluorine, chlorine, OH, $NO_2$, Si-alkyl$_3$-$(C_1-C_4)$, $CF_3$, CN, $SO_3H$, N-alkyl$_2$-$(C_1-C_4)$, CO-phenyl, COO-phenyl, COO-aryl-$(C_6-C_{10})$, CO-aryl-$(C_6-C_{10})$, PO-phenyl$_2$, POalkyl$_2$-$(C_1-C_4)$, PO(O-alkyl-$(C_1-C_6)$)$_2$, Si(alkyl)$_3$-$(C_1-C_8)$, where alkyl and aryl are as defined above.

In these ligands, $R^6$ and $R^7$ and/or $R^8$ and $R^9$ may also be linked by a covalent bond so as to form a cyclic compound having from five to seven atoms.

Typical representatives of the ligand systems used in the process of the invention are phosphine and diphosphine ligands and modifications of this ligand type, for example dppb (1,4-bis(diphenylphosphino)butane), dcypb (1,4-bis(dicyclohexylphosphino)butane), bppm (2-diphenylphosphino-methyl-4-diphenylphosphino-1-tert-butoxycarbonylpyrrolidine), diop (2,3-O-isopropylidene-2, 3-dihydroxy-1,4-bis(diphenylphosphino)butane) (Kagan et al., J. Amer. Chem. Soc. (1972), 94, 6429), (2R,3R,5R,6R)-2,3-dimethoxy-2,3-dimethyl-5,6-bis (diphenylphosphinomethyl)-1,4-dioxane (Berens et al., J. Org. Chem. (1995), 60, 8204), TPPTS (tris-(3-sulfophenyl) phosphine trisodium salt) (Herrmann et al., Angew. Chem., Int. Ed. Engl. (1995), 34, 811), BINAS (2,2'-bis[[bis(3-sulfophenyl)phosphino]methyl]-4,4',7,7'-tetrasulfo-1,1'-binaphthyl octasodium salt) (Herrmann et al., Inorg. Synth. (1998), 32, 8), diphosphinite ligands based on carbohydrates as described, for example, in DD 140036 and WO 95/18787 and related ligand systems such as dpoe (1,2-bis (diphenylphosphinoxy)ethane), bdpch ((1R,2R)-(trans)-1,2-bis-(diphenylphosphinoxy)cyclohexane) and aminophosphine phosphinites (Agbossou et al., Coordination Chemistry Rev. 1998, 178–180, 1615), e.g. the PROPRAHOS analog (2R)-1-[[(diphenyl-phosphino)(cyclopenthyl) amino]methyl]-2-diphenylphosphinoxy-3-(1-naphthalenyloxy)propane (Krause et al., J. Mol. Catal. A: Chem. (1995), 104, 147) and aminophosphines, e.g. (4S)-2-(2-(diphenylphosphino)phenyl)-4-isopropyl-1,3-oxazoline (Koch G., Lloyd-Jones G. C., Loiseleur O., Pfaltz A., Pretot R., Schaffner S., Schnider P., von Matt P. Recl. Trav. Chim. Pays-Bas 1995, 114, 206–10).

The phosphorus-containing ligands can be prepared under conditions with which those skilled in the art are familiar (for example by methods as are described in Chemistry of Organophosphorus Compounds, Ed. F. R. Hartley, Serial Ed. S. Patai, Vol. 1, John Whiley, 1990). Some of the ligands and/or metal complexes are commercially available (for example from Aldrich or Strem/ABCR).

The catalytically active metal complexes can be synthesized by, for example, reacting the phosphorus-containing ligands in a known manner (EP-A-0158875; EP-A-0437690) with rhodium, iridium, ruthenium, palladium, platinum, cobalt or nickel complexes containing labile ligands (e.g. [Rh(COD)$_2$]BF$_4$, [RuCl$_2$(COD)]$_n$, [Ir(COD) Cl]$_2$). Furthermore, all methods with which an organometallic chemist is familiar can be utilized for generating appropriate complexes.

The catalysts can be produced in situ from the metal precursor and the ligand, or they are used in isolated form.

The process of the invention is generally carried out at a temperature of −40–100° C., preferably at −20–60° C.

The initial hydrogen pressure in the process of the invention can be varied in a wide range from 0.1 bar to 300 bar. The process is preferably carried out at 1 bar–100 bar, particularly preferably from 20 to 60 bar.

It can be advantageous to carry out the process of the invention in the presence of additives.

Additives are acids such as p-toluenesulfonic acid, tetrafluoroboric acid, phosphoric acid, sulfuric acid or acetic acid, bases such as sodium hydroxide, potassium hydroxide, tertiary amines, proton sponges, cesium carbonate, acetate or sodium carbonate, salts such as halides of the alkali metals or ammonium halides, phase transfer catalysts, surfactants or cyclodextrins, which are employed in amounts of 0–100 mol % based on the amine (II) used.

Preferred solvents for the reductive amination are alcohols, in particular $C_1-C_6$-alkanols, particularly preferably methanol, ethanol, propanol, isopropanol, or else water and mixtures thereof. In the case of sparingly soluble substrates, solvent mixtures of alcohols and halogenated hydrocarbons and/or ethers, in particular cyclic ethers such as THF, and/or aromatic hydrocarbons such as toluene are also useful.

The process can also be carried out in a 2-phase system as described, for example, in DE 19737053.

The catalyst is usually used in amounts of from 0.001 to 5 mol %, preferably from 0.001 to 0.01 mol %, based on the carbonyl component of the formula (I).

The following examples illustrate the invention without restricting it to them.

EXAMPLE 1

In an autoclave, a solution of 5.0 mmol of acetophenone, 5.0 mmol of piperidine and 0.01 mmol of Rh[(dppb)(COD)]BF$_4$ in 10 ml of methanol was stirred at room temperature and an initial hydrogen pressure of 51–52 bar for 19.7 hours. Under these conditions, 25.4% of the ketone were reacted. The ratio of 1-N-piperidinylethylbenzene to 1-phenylethylcarbinol in the product determined by $^1$H-NMR spectroscopy was 1/10 (cf. Table 1).

EXAMPLE 2

In an autoclave, a solution of 5.0 mmol of acetophenone, 5.0 mmol of piperidine, 0.2 mmol of p-toluenesulfohic acid and 0.01 mmol of Rh[(dppb)(COD)]BF$_4$ in 10 ml of methanol was stirred at room temperature and an initial hydrogen pressure of 51–52 bar for 16 hours. Under these conditions, 5.6% of the ketone were reacted. The ratio of 1-N-piperidinylethylbenzene to 1-phenylethylcarbinol in the product was 2/1 (cf. Table 1).

EXAMPLE 3

In an autoclave, a solution of 5.0 mmol of acetophenone, 5.0 mmol of benzylamine and 0.01 mmol of Rh[(dppb)(COD)]BF$_4$ in 10 ml of methanol was stirred at room temperature and an initial hydrogen pressure of 51–52 bar for 20 hours. Under these conditions, 10.7% of the ketone were reacted. The ratio of 1-N-piperidinylethylbenzene to 1-phenylethylcarbinol in the product was 1/10 (cf. Table 1).

EXAMPLE 4

A solution of 60 mmol of acetophenone in 40 ml of toluene, 40 ml of 25% strength aqueous ammonia solution, 0.15 mmol of [Ir[(COD)Cl]$_2$ and 6 ml of a 0.1 molar solution of 2,2'-bis[[bis(3-sulfophenyl)phosphino]methyl]-4,4',7,7'-tetrasulfo-1,1'-binaphthyl octasodium salt (BINAS) were introduced into a 300 ml autoclave provided with an intensive magnetic stirrer and were stirred at 130° C. and an initial hydrogen pressure of 46 bar. After 13 hours, the autoclave was cooled and vented, the organic phase was dried over MgSO$_4$ and analyzed by gas chromatography. After evaporation of the solvent, the residue was examined by NMR spectroscopy. At a conversion of 38%, the ratio of 1-phenylethylamine to 1-phenylethanol was found to be 7/31 (cf. Table 1).

EXAMPLE 5

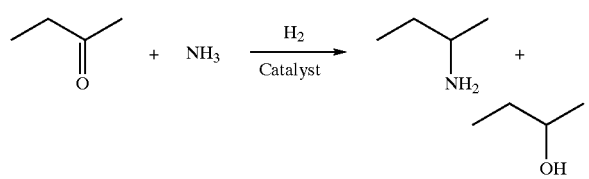

A solution of 60 mmol of 2-octanone in 40 ml of heptane, 40 ml of 25% strength aqueous ammonia solution, 0.15 mmol of [Ir[(COD)Cl]$_2$, 2.4 mmol of partially methylated β-cyclodextrin from Cyclolab (Budapest, Hungary) and 6 ml of a 0.1 molar solution of 2,2'-bis[[bis(3-sulfophenyl)phosphino]-methyl]-4,4',7',7'-tetrasulfo-1,1'-binaphthyl octasodium salt (BINAS) were introduced into a 300 ml autoclave provided with intensive magnetic stirring and were stirred at 130° C. and an initial hydrogen pressure of 89 bar. After 7 hours, the autoclave was cooled and vented, the organic phase was dried over MgSO$_4$ and analyzed by gas chromatography. After evaporation of the solvent, the residue was examined by NMR spectroscopy. At a conversion of 10%, the ratio of 2-octylamine to 2-octanol was found to be 7/3.

EXAMPLE 6

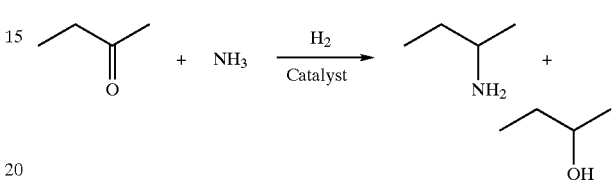

0.15 mol of butanone, 60 ml of 25% strength aqueous ammonia solution, 0.15 mmol of [Ir[(COD)Cl]2 and 6 ml of a 0.1 molar solution of BINAS were introduced into a 100 ml autoclave provided with intensive magnetic stirring and were stirred at 130° C. and an initial hydrogen pressure of 110 bar. After 5 hours, the autoclave was cooled and vented, and the aqueous solution was examined by NMR spectroscopy. At a conversion of 80%, the ratio of 2-butylamine to 2-butanol was found to be 1/2. The proportion of the secondary amine was 6%.

EXAMPLE 7

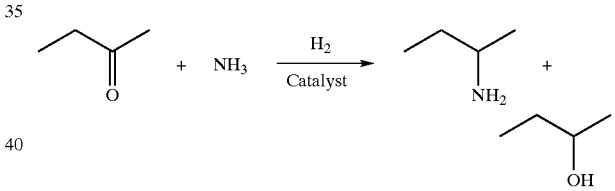

0.15 mol of butanone, 50 ml of 25% strength aqueous ammonia solution, 0.15 mmol of [Rh[(COD)Cl]$_2$ and 6 ml of a 0.1 molar solution of BINAS were introduced into a 100 ml autoclave provided with an intensive magnetic stirrer and were stirred at 100° C. and an initial hydrogen pressure of 63 bar. After 7 hours, the autoclave was cooled and vented, the aqueous solution (13% of starting material, 14% of 2-butanol and 73% of 2-butylamine) was extracted with ether a number of times, the organic phase was dried over caustic potash and fractionated via a 30 cm Vigreux column. The fraction between 55 and 66° C. (10.2 g) had a content of the desired 2-butylamine of 30% (GC analysis).

EXAMPLES 8 to 13

These examples were carried out in a manner analogous to Examples 1–3. Amine components, catalysts and the results of the reaction are indicated in Table 2.

EXAMPLE 14

In a 100 ml autoclave fitted with a dropping funnel, 5.1 ml (50 mmol) of benzaldehyde were admixed with 20 ml of methanol which had been saturated with ammonia at 10° C. The autoclave was closed, pressurized with 91 bar of hydrogen and heated to 80° C. A solution of 0.05 mmol of [Rh(dcypb)]BF$_4$ in 10 ml of methanol was subsequently added from the dropping funnel and the mixture was stirred at 80° C. for another 2 hours. After cooling and evaporation of the solvent, the residue was analyzed by gas chromatography and NMR spectroscopy. At a conversion of above 99%, the ratio of benzylamine to dibenzylamine to benzyl alcohol was found to be 25/32/43.

EXAMPLE 15

0.2 ml (2 mmol) of benzaldehyde were dissolved in 2 ml of heptane and, after addition of a solution of 23 mg (0.04 mmol) of tris-(3-sulfophenyl)phosphine trisodium salt (TPPTS) and 7.2 mg (0.02 mmol) of [Rh[(C$_8$H$_{14}$)$_2$Cl]$_2$ in 2 ml of 25% strength aqueous ammonia solution, hydrogenated at 46 bar and 90° C. while stirring vigorously in an autoclave. After 8 hours, the autoclave was cooled and vented, the organic phase was dried over MgSO$_4$ and analyzed by gas chromatography. At a conversion of above 99%, the ratio of benzylamine to dibenzylamine to benzyl alcohol was found to be 52/20/18.

EXAMPLE 16

This example was carried out in a manner analogous to Example 14. The reaction conditions and results are reported in Table 2.

EXAMPLE 17

In a 100 ml autoclave fitted with a dropping funnel, a solution of 5.1 ml (50 mmol) of benzaldehyde in 15 ml of ethanol was admixed with 20 ml of 25% strength ammonia solution. The autoclave was closed, pressurized with 78 bar of hydrogen and heated to 100° C. A solution of 0.1 mmol of [Rh(dppb)]BF$_4$ in 10 ml of methanol was subsequently added from the dropping funnel and the mixture was stirred at 100° C. for another 2 hours. After cooling and evaporation of the solvent, the residue was analyzed by gas chromatography and NMR spectroscopy. At a conversion of above 99%, the ratio of benzylamine to benzyl alcohol was found to be 15/85.

EXAMPLE 18

In a 100 ml autoclave fitted with a dropping funnel, a solution of 5.1 ml (50 mmol) of benzaldehyde in 10 ml of methanol was admixed with 20 ml of 25% strength: ammonia solution. The autoclave was closed, pressurized with 69 bar of hydrogen and heated to 90° C. A solution of 0.05 mmol of [Rh[(COD)Cl]$_2$ and 0.2 mmol of 2,2'-bis[[bis(3-sulfophenyl)phosphino]methyl]-4,4',7,7'-tetrasulfo-1,1'-binaphthyl octasodium salt (BINAS) in 5 ml of 5% strength aqueous ammonia solution was subsequently added from the dropping funnel and the mixture was stirred at 90° C. for another 1.5 hours. After cooling and evaporation of the solvent, the residue was analyzed by gas chromatography and NMR spectroscopy. At a conversion of 99%, the ratio of benzylamine to dibenzylamine to benzyl alcohol was found to be 58/25/17.

EXAMPLE 19

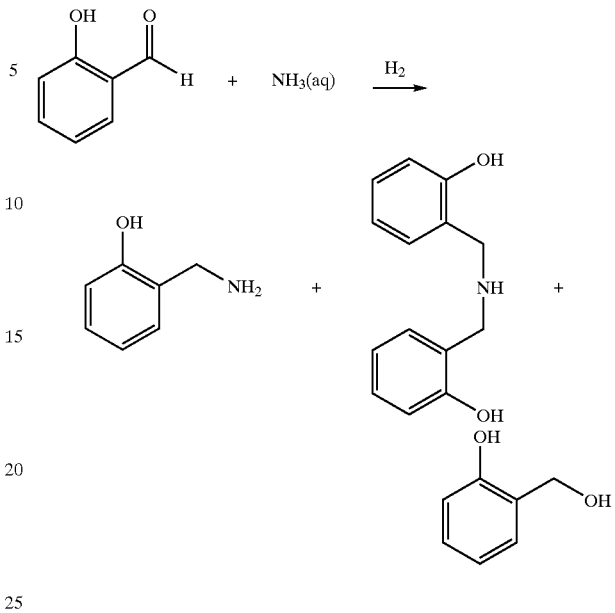

In a 100 ml autoclave fitted with a dropping funnel, a solution of 5.3 ml (50 mmol) of salicylaldehyde in 30 ml of ethanol was added dropwise to 10 ml of 25% strength ammonia solution while stirring. The autoclave was closed, pressurized with 58 bar of hydrogen and heated to 90° C. A solution of 0.05 mmol of [Rh[(COD)Cl]$_2$ and 0.2 mmol of 2,2'-bis[[bis(3-sulfophenyl)phosphino]methyl]-4,4',7,7'-tetrasulfo-1,1'-binaphthyl octa-sodium salt (BINAS) in 5 ml of 5% strength aqueous ammonia solution was subsequently, added from the dropping funnel and the mixture was stirred at 90° C. for another 10 hours. After cooling and evaporation of the solvent, the residue was analyzed by NMR spectroscopy. At a conversion of 96%, the ratio of o-hydroxybenzylamine to di(o-hydroxybenzyl)amine was found to be 51/45.

EXAMPLE 20

In a 30 ml autoclave fitted with a dropping funnel, a solution of 0.01 mmol of Rh[(dppb)COD]BF$_4$ in 5 ml of methanol was hydrogenated at room temperature and a hydrogen pressure of 50 bar for 15 minutes. A solution of 5 mmol of 4-hydroxybenzaldehyde and 10 mmol of piperidine in 10 ml of methanol was subsequently added from the dropping funnel and hydrogenation was continued for a further 2 hours. After evaporation of the solvent, the residue was examined by NMR spectroscopy. At a conversion of above 99%, the ratio of: N-(4-hydroxybenzyl)piperidine to 4-hydroxybenzyl alcohol was found to be 94/1.

EXAMPLES 21 to 28

These examples were carried out in a manner analogous to Example 20. Aldehydes and the results of the reactions are reported in Table 3.

EXAMPLES 29 to 34

These examples were carried out in a manner analogous to Example 1. Catalysts and the results of the reactions are reported in Table 4.

EXAMPLE 35

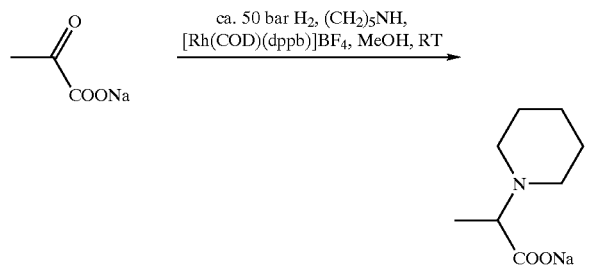

In an autoclave, a solution of 5.0 mmol of sodium pyruvate, 5.0 mmol of piperidine and 0.01 mmol of Rh[(dppb)COD]BF$_4$ in 10 ml of MeOH was stirred at room temperature and an initial hydrogen pressure of 51–52 bar for 89 hours. Under these conditions, 82% of the keto acid were reacted. The ratio of sodium N,N-pentamethylenealaninate to sodium lactate in the product determined by $^1$H-NMR spectroscopy was 9.2/1.

EXAMPLE 36

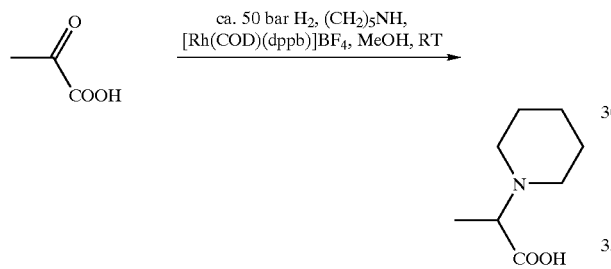

In an autoclave, a solution of 5.0 mmol of pyruvic acid, 5.0 mmol of piperidine and 0.01 mmol of Rh[(dppb)COD]BF$_4$ in 10 ml of MeOH was stirred at room temperature and an initial hydrogen pressure of 51–52 bar for 20 hours. Under these conditions, 99.6% of the keto acid were reacted. The ratio of N,N-pentamethylenealanine to lactic acid in the product determined by $^1$H-NMR spectroscopy was 1.4/1.

EXAMPLE 37

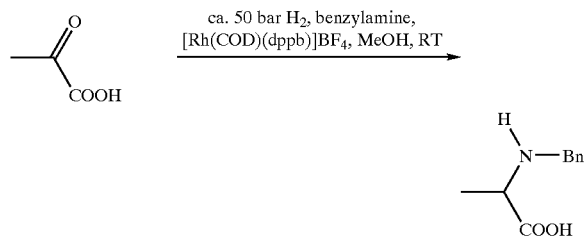

In an autoclave, a solution of 5.0 mmol of pyruvic acid, 5.0 mmol of benzylamine and 0.01 mmol of Rh[(dppb)COD]BF$_4$ in 10 ml of MeOH was stirred at room temperature and an initial hydrogen pressure of 51–52 bar for 20 hours. Under these conditions, 94% of the keto acid were reacted. N-Benzylalanine is insoluble in the reaction mixture and could be separated off by filtration. Washing with MeOH and ether gave the pure product (m.p. 238–239° C.).

EXAMPLE 38

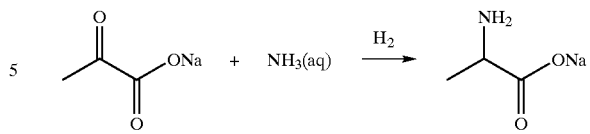

A solution of 3.3 g (30 mmol) of sodium pyruvate in 40 ml of 25% strength ammonia solution was placed in a 100 ml autoclave fitted with a dropping funnel. The autoclave was closed, pressurized with 33 bar of hydrogen and heated to 60° C. A solution of 0.15 mmol of [Rh[(COD)Cl]$_2$ and 0.6 mmol of 2,2'-bis[[bis(3-sulfophenyl)phosphino]methyl]-4, 4',7,7'-tetrasulfo-1,1'-binaphthyl octasodium salt (BINAS) in 10 ml of 25% strength aqueous ammonia solution was subsequently added from the dropping funnel and the mixture was stirred at 60° C. for 16 hours. After cooling and venting the autoclave, the excess ammonia was taken off under reduced pressure, and the remaining mixture was neutralized with 10% strength hydrochloric acid until neutral to bromothymol blue, introduced onto an ion exchange column (Dowex AG 50W-X8, H form, 200–400 mesh, 25×2 cm), washed with 100 ml of water and eluted with 5% strength aqueous ammonia. Evaporation under reduced pressure gave 2.0 g (75%) of alanine as a colorless crystalline residue.

EXAMPLE 39

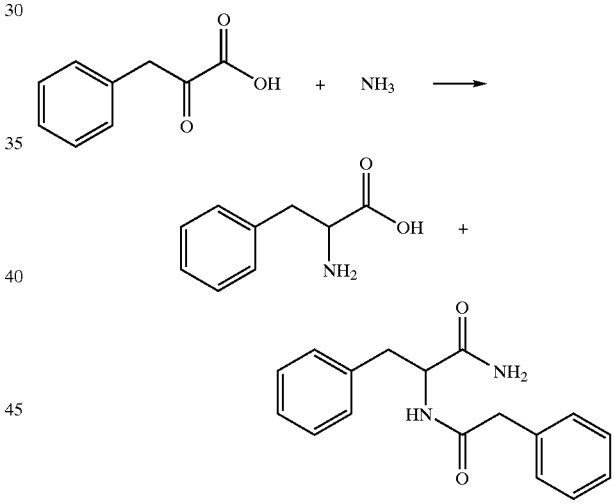

A solution of 5 g (30 mmol) of phenylpyruvic acid in 50 ml of ethanol, 20 ml of 25% strength aqueous ammonia solution, 0.15 mmol of [Rh[(COD)Cl]$_2$ and 6 ml of a 0.1 molar solution of 2,2'-bis[[bis(3-sulfophenyl)phosphino] methyl]-4,4',7,7'-tetrasulfo-1,1'-binaphthyl octasodium salt (BINAS) were introduced into a 300 ml autoclave provided with an intensive magnetic stirrer and were stirred at 60° C. and an initial hydrogen pressure of 42 bar. After 24 hours, the autoclave was cooled and vented. N-Phenylacetylphenylalaninamide is insoluble in the reaction mixture and could be separated off by filtration. Washing with water and alcohol gave 1.8 g (43%) of pure N-phenylacetylphenylalaninamide. The excess ammonia was removed from the mother liquor under reduced pressure. The aqueous solution was neutralized with 10% strength hydrochloric acid until neutral to bromothymol blue and rinsed onto a column of Dowex (AG 50W-X8, H form, 200–400 mesh 25×2 cm), washed with 100 ml of water and eluted with 5% strength aqueous ammonia. Evaporation under reduced pressure gave 0.72 g (15%) of phenylalanine as a colorless crystalline residue.

EXAMPLE 40

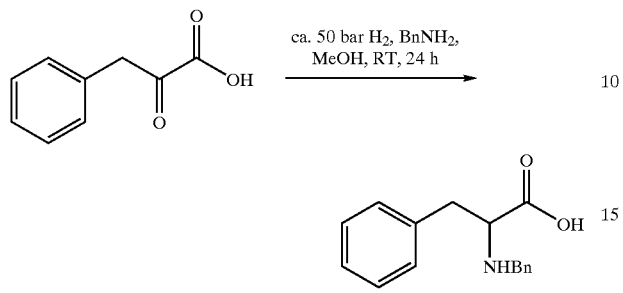

In an autoclave, a solution of 5.0 mmol of phenylpyruvic acid, 5.0 mmol of benzylamine and 0.01 mmol of Rh[(dppb)(COD)]BF$_4$ in 10 ml of MeOH was stirred at room temperature and an initial hydrogen pressure of 52 bar for 20 hours. Under these conditions, 99% of the keto acid were reacted. N-Benzylphenylalanine is insoluble in the reaction mixture and could be separated off by filtration. Washing with MeOH and ether gave the pure N-benzylphenylalanine (m.p. 219–220° C.). Yield: 0.90 g (71%).

EXAMPLES 41 to 44

These examples were carried out in a manner analogous to Example 40. Chiral ligands and the yields and enantioselectivities are indicated in Table 5.

TABLE 1

Overview of the reductive amination of acetophenone

| Example | Catalyst | Amine (acetophenone:amine) | Time (h) | Conversion of RR'C=O (%) | C—N/C—OH ratio |
|---|---|---|---|---|---|
| 1[a] | Rh[(dppb)COD]BF$_4$[b] | (CH$_2$)$_5$NH (1:1) | 19.7 | 25.4 | 0.1 |
| 2[a] | Rh[(dppb)COD]BF$_4$[b] | (CH$_2$)$_5$NH (1:1)[c] | 16 | 5.6 | 2 |
| 3[a] | Rh[(dppb)COD]BF$_4$[b] | BnNH$_2$ (1:1) | 20 | 10.7 | 0.1 |
| 4[d] | [Ir(COD)Cl]$_2$/BINAS[e] (1:4) | NH$_3$ (1:10) | 13 | 38 | 0.22 |

[a]Conditions: RT, 51–52 bar (initial pressure), 5.0 mmol of acetophenone, 5.0 mmol of amine, 0.01 mmol of precatalyst, 10 ml of MeOH;
[b]dppb = 1,4-bis(diphenylphosphino)butane;
[c]TsOH as additive (molar ratio of additive:cat. = 20:1);
[d]Conditions: 130° C. 46 bar (initial pressure), 60 mmol of acetophenone, 40 ml of 25% strength aqueous ammonia solution, 0.01 mmol of precatalyst, 40 ml of toluene;
[e]BINAS = 2,2'-bis[[bis(3-sulfophenyl)phosphino]methyl]-4,4',7,7'-tetrasulfo-1,1'-binaphthyl octasodium salt.

TABLE 2

Reductive amination of benzaldehyde

| Example | Catalyst | Amine (sub./amine) | Solvent | Additive | Temp./Pressure | Time (h) | Conversion of RR'C=O (%) | C—N (prim:sec)/C—OH |
|---|---|---|---|---|---|---|---|---|
| 8 | Rh(PPh$_3$)$_3$Cl | (CH$_2$)$_5$NH (1:1) | MeOH | — | RT/52 | 20 | 94.5 | 0.13 |
| 9 | [Rh(dppb)(COD)]BF$_4$[b] | (CH$_2$)$_5$NH (1:1) | MeOH | — | RT/52 | 20 | >99.9 | 1.5 |
| 10 | [Rh(dppb)(COD)]BF$_4$[b] | (CH$_2$)$_5$NH (1:1) | MeOH | TsOH[a] | RT/52 | 20 | >99.9 | 1.3 |
| 11 | [Rh(DPOE)(COD)]BF$_4$[c] | (CH$_2$)$_5$NH (1:1) | MeOH | — | RT/52 | 20 | >99.9 | 1.8 |
| 12 | [Rh(DPOE)(COD)]BF$_4$[c] | (CH$_2$)$_5$NH (1:1) | MeOH | TsOH[a] | RT/52 | 20 | >99.9 | 1.4 |
| 13 | [Rh(dppb)(COD)]BF$_4$[b] | BnNH$_2$ (1:1) | MeOH | — | RT/52 | 20 | 38.7 | nur Amin |
| 14 | [(Rh(dcypb)(COD)]BF$_4$[g] | NH$_3$ (1:6) | MeOH | — | 80/100 | 2 | >99 | 1.4 (5:6) |
| 15 | [(Rh(COD)Cl$_2$]$_2$/TPPTS[d] (1:4) | NH$_3$ (1:7) | Hept./H$_2$O | — | 90/46 | 8 | >99 | 4 (5:2) |
| 16 | [(Rh(COD)Cl$_2$]$_2$/BINAS[e] (1:4) | NH$_3$ (1:7) | Tol./H$_2$O | BnNMe$_3$Cl[f] | 100/120 | 3 | >99 | 1 (5:1) |
| 17 | [Rh(dppb)(COD)]BF$_4$[b] | NH$_3$ (1:6) | EtOH/H$_2$O | — | 100/79 | 2 | >99 | 0.2 (1:0) |

TABLE 2-continued

Reductive amination of benzaldehyde

| Example | Catalyst | Amine (sub./amine) | Solvent | Additive | Temp./Pressure | Time (h) | Conversion of RR'C=O (%) | C—N (prim:sec)/C—OH |
|---|---|---|---|---|---|---|---|---|
| 18 | [(Rh(COD)Cl$_2$]$_2$/BINAS$^e$ (1:4) | NH$_3$ (1:8) | MeOH/H$_2$O | — | 90/69 | 1.5 | >99 | 5 (12:5) |

[a] Molar ratio of TsOH:cat. = 20:1;
[b] dppb = 1,4-bis(diphenylphosphino)butane;
[c] DPOE = 1,2-bis(diphenylphosphinoxy)ethane;
[d] TPPTS = tris-(3-sulphophenyl)phosphine trisodium salt;
[e] BINAS = 2,2'-bis[[bis(3-sulfophenyl)phosphino]methyl]-4,4',7,7'-tetrasulfo-1,1'-binaphthyl octasodium salt;
[f] molar ratio of BnNMe$_3$Cl:cat. = 10:1;
[g] dcypb = 1,4-bis(dicyclohexylphosphino)butane.

TABLE 3

Reductive amination of aldehydes with piperidine[a]
ca. 50 bar H$_2$, (CH$_2$)$_5$NH,
RCHO $\xrightarrow[\text{[Rh(dppb)]BF4.}]{\text{MeOH, RT, 2 h}}$ RCH$_2$N(CH$_2$)$_5$ + RCH$_2$OH

| Example | Aldehyde | C—N/C—OH |
|---|---|---|
| 20 | 4-HOC$_6$H$_4$CHO | 94 |
| 21 | 2-MeC$_6$H$_4$CHO | 50 |
| 22 | 4-MeOC$_6$H$_4$CHO | 12 |
| 23 | C$_6$H$_4$CHO | 8.6 |
| 24 | 4-ClC$_6$H$_4$CHO | 6.7[b] |
| 25 | 4-NO$_2$C$_6$H$_4$CHO | c |
| 26 | PhCHMeCHO | 7.5 |
| 27 | EtCHMeCHO | 18 |
| 28 | n-C$_7$H$_{15}$CHO | 210 |

[a] For conditions see Example 20;
[b] ca. 40% of 4-ClC$_6$H$_4$CH(OMe)$_2$;
[c] no reaction product, ca. 40% of 4-NO$_2$C$_6$H$_4$CH(OMe)$_2$

TABLE 5

Enantioselective synthesis of N-benzylphenylalanine[a]

ca. 50 bar H$_2$, BnNH$_2$, MeOH, RT, 20–24 h, [Rh(COD)(P-P*)]BF4.

| Example | Ligand (P-P*) | Yield | Ee[b] | Configuration |
|---|---|---|---|---|
| 41 | | 59 | 38 | R |
| 42 | R-DIOP[d] | 51 | 10 | S |

TABLE 4

Reductive amination of 2-phenylpropanal[a]
ca. 50 bar H$_2$, RR'NH, cat., MeOH, RT

| Example | Catalyst | Amine (amine:C=O) | Additive (ad:cat) | Conversion of RR'C=O (%)[b] | C—N/C—OH |
|---|---|---|---|---|---|
| 29 | Rh(PPh$_3$)$_3$Cl | (CH$_2$)$_5$NH (1:1) | — | 70.3 | 0.45 |
| 30 | Rh[(dppb)COD]BF$_4$[c] | (CH$_2$)$_5$NH (1:1) | — | >99.9 | 1.8 |
| 31 | Rh[(dppb)COD]BF$_4$[c] | (CH$_2$)$_5$NH (2:1) | — | >99.9 | 1.9 |
| 32 | Rh[(dppb)COD]BF$_4$[c] | (CH$_2$)$_5$NH (1:1) | TsOH (20:1) | >99.9 | 4.8 |
| 33 | Rh[(DPOE)COD]BF$_4$[d] | (CH$_2$)$_5$NH (1:1) | — | >99.9 | 6.8 |
| 34 | Rh[(DPOE)COD]BF$_4$[d] | (CH$_2$)$_5$NH (1:1) | TsOH (20:1) | >99.9 | 3.2 |

[a] For conditions see Table 1;
[b] Conversion after 20 h;
[c] dppb = 1,4-bis(diphenylphosphino)butane;
[d] DPOE = 1,2-bis(diphenylphosphinoxy)ethane.

TABLE 5-continued

Enantioselective synthesis of N-benzylphenylalanine[a]

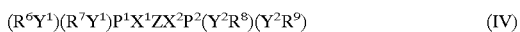

| Example | Ligand (P-P*) | Yield | Ee[b] | Configuration |
|---|---|---|---|---|
| 43 | R-Bdpch[e] | 58 | 17 | R |
| 44 | R-Cyclopentyl-ppp[f] | 63 | 12 | S |

[a]For conditions see Example 40;
[b]GC analysis on the chiral column L-Chirasill-Val;
[c](2R, 3R, 5R, 6R)-2,3-dimethoxy-2,3-dimethyl-5,6-bis (diphenylphosphinomethyl)-1,4-dioxane;
[d](4R, 5R)-4,5-bis-(diphenylphosphinomethyl)2,2-dimethyl-1,3-dioxolane;
[e](1R, 2R)-1,2-bis(diphenylphosphinoxy)cyclohexane;
[f](2R)-1-[[(diphenylphosphino)(cyclopentyl)amino]methyl]-2-diphenylphosphinoxy-3-(1-naphthalenyloxy)propane

What is claimed is:

1. A process for preparing amines of the formula (III)

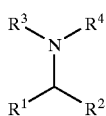   (III)

by reacting a compound of the formula (I)

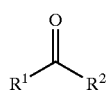   (I)

with a compound of the formula (II)

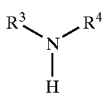   (II)

which is carried out at a temperature of −40–100° C., where the radicals $R^1$ to $R^4$ are selected independently from the group consisting of hydrogen, $(C_1-C_{24})$-alkyl, $(C_2-C_{24})$-alkenyl, $(C_2-C_{24})$-alkynyl, $(C_6-C_{10})$-aryl, $CF_3$, CHO, $SO_3H$, COO-alkyl-$(C_1-C_8)$, $CONH_2$, CONHalkyl-$(C_1-C_8)$, CONalkyl$_2$—$(C_1-C_8)$, CO-alkyl-$(C_1-C_8)$, CO-phenyl, COO-phenyl, COO-aryl-$(C_6-C_{10})$, CO-aryl-$(C_6-C_{10})$, P(aryl)$_2$, Palkyl$_2$-$(C_1-C_8)$, PO(aryl)$_2$, POalkyl$_2$—$(C_1-C_4)$, $PO_3H_2$, POalkyl-$(C_1-C_4)$(O-alkyl-$(C_1-C_6)$), PO(O-alkyl-$(C_1-C_6))_2$, $SO_3$-alkyl-$(C_1-C_4)$, $SO_2$-alkyl-$(C_1-C_6)$, SO-alkyl-$(C_1-C_6)$ and Si(alkyl)$_3$—$(C_1-C_8)$, where alkyl is, for the purposes of the present invention, an unbranched or branched aliphatic or cyclic radical, alkenyl is an olefinic hydrocarbon, alkynyl is an acetylenic hydrocarbon and aryl is an aromatic radical, alkyl, alkenyl, alkynyl and also aryl may bear substituents selected independently from among hydrogen, O-alkyl-$(C_1-C_8)$, OCO-alkyl-$(C_1-C_8)$, O-phenyl, phenyl, aryl $(C_6-C_{10})$, fluorine, chlorine, bromine, iodine, OH, $NO_2$, $CF_3$, CHO, $SO_3H$, $NH_2$, NH-alkyl-$(C_1-C_8)$, N-alkyl$_2$-$(C_1-C_8)$, NHCO-alkyl-$(C_1-C_4)$, CO-phenyl, COO-alkyl-$(C_1-C_8)$, $CONH_2$, CO-alkyl-$(C_1-C_8)$, NHCOH, NHCOO-alkyl-$(C_1-C_4)$, CO-phenyl, COO-phenyl, COO-aryl-$(C_6-C_{10})$, CO-aryl-$(C_6-C_{10})$, CHCH—$CO_2$-alkyl-$(C_1-C_8)$, P(aryl)$_2$, CHCHCO$_2$H, P-alkyl$_2$—$(C_1-C_8)$, PO-aryl$_2$, POalkyl$_2$—$(C_1-C_4)$, $PO_3H_2$, POalkyl-$(C_1-C_4)$(O-alkyl-$C_1-C_6$)), PO(O-alkyl-$(C_1-C_6))_2$, $SO_3$-alkyl-$(C_1-C_4)$, $SO_2$-alkyl-$(C_1-C_6)$, SO-alkyl-$(C_1-C_6)$ and Si(alkyl)$_3$—$(C_1-C_8)$, both $R^1$ and $R^2$ and also $R^3$ and $R^4$ can be linked by covalent bonds so that $R^1$ and $R^2$ and/or $R^3$ and $R^4$ in each case form a four- to eight-membered ring, where $R^1$ or $R^2$ may also be part of an organometallic compound, in the presence of hydrogen and a homogeneous catalyst system comprising at least one metal atom selected from the group consisting of Rh, Ru, Ir, Pd, Pt, Co and Ni and one or more monodentate or bidentate achiral or chiral ligands of the formula (IV) or (V)

$(R^6Y^1)(R^7Y^1)P^1X^1ZX^2P^2(Y^2R^8)(Y^2R^9)$ (IV)

$(R^6Y^1)(R^7Y^1)(R^8Y^1)P$ (V)

where $R^6$ to $R^9$ are identical or different and are each a hydrogen atom, $C_1-C_{24}$-alkyl, $C_2-C_{20}$-alkenyl, $C_3-C_8$-cycloalkyl, $C_5-C_8$-cycloalkenyl, $C_6-C_{14}$-aryl, phenyl, naphthyl, fluorenyl, and in which all the abovementioned substituents may each be substituted by one or more substituents selected independently from among hydrogen, $C_1-C_{20}$-alkyl, $C_2-C_{20}$-alkenyl, $C_1-C_{10}$-haloalkyl, $C_3-C_8$-cycloalkyl, $C_5-C_8$-cycloalkenyl, $C_2-C_9$-heterocycloalkyl, $C_1-C_9$-heterocyclo-alkenyl, $C_6-C_{14}$-aryl, phenyl, $C_1-C_{10}$-alkoxy, OCO-alkyl-$(C_1-C_8)$, O-aryl-$(C_5-C_{10})$, O-phenyl, $C_1-C_9$-trihalomethylalkyl, fluoro, chloro, bromo, iodo, nitro, hydroxy, trifluoromethylsulfonato, oxo, thio, thiolato, amino, $C_1-C_8$-substituted amino of the types mono- and di-$C_1-C_8$-alkylamino or $C_2-C_8$-alkenylamino or mono-, di-, tri-$C_6-C_8$-arylamino or $C_1-C_8$-alkyl-$C_6-C_8$-arylamino, NH—CO-alkyl-$C_1-C_8$, NH—CO-aryl-$C_6-C_8$, cyano, $C_1-C_8$-acyloxy, carboxyl, carboxylato of the formula $COOR^{12}$, sulfinato, sulfonato of the formula $SO_3R^{12}$, phosphonato of the formula $PO_3H_2$, $PO_3HR^{12}$, $PO_3R^{12}$, where $R^{12}$ is either a monovalent cation, $NH^{4+}$, $N(C_1-C_{10}$-alkyl)$_4^+$, $N(C_1-C_{10}$-alkyl/$C_6-C_{10}$-aryl)$_4$+, $C_1-C_{18}$-alkyl or $C_6$-aryl, tri-$C_1-C_6$-alkylsilyl, and where two of these substituents may also be bridged, $X^1$ and $X^2$ are each, independently of one another, a direct phosphorus-carbon bond, O, S or $NR^{10}$, where $R^{10}$ corresponds to one of the radicals defined for $R^6-R^9$, $Y^1$ and $Y^2$ is a direct phosphorus-carbon bond, —O— or —$NR^{11}$—, where $R^{11}$ corresponds to one of the radicals defined for $R^6-R^9$, Z corresponds to 1–6 carbon atoms which are bound to one another by single or multiple bonds and connect the unit $(R^6Y^1)(R^7Y^1)PX^1$ to the unit $X^2P(Y^2R^8)(Y^2R^9)$, where Z may be part of an aliphatic, cycloaliphatic, olefinic, cycloolefinic system which may contain from one to four heteroatoms from the group consisting of N, O, S, a metallocene, in particular a ferrocene, a 1,1'-disubstituted ferrocene, 1-(1-ethylenyl)-2-ferrocenyl or a 1,2-disubstituted ferrocene, or one or more aromatic or heteroaromatic ring systems, where the ring system comprises a total of from 2 to 14 carbon atoms which may be monosubstituted or polysubstituted by substituents as specified for $R^6$–$R^9$ or directly by $C_1$–$C_{10}$-alkoxy, OCO-alkyl-($C_1$–$C_8$), O-aryl-($C_5$–$C_{10}$), O-phenyl, $C_1$–$C_9$-trihalomethylalkyl, trifluoromethyl, trichloromethyl, fluoro, chloro, bromo, iodo, nitro, hydroxy, trifluoromethylsulfonato, oxo, thio, thiolato, amino, $C_1$–$C_8$-substituted amino of the formulae $NH_2$, NH-alkyl-$C_1$–$C_8$, NH-aryl-$C_5$–$C_6$, N-alkyl$_2$—$C_1$–$C_8$, N-aryl$_2$—$C_5$–$C_6$, N-alkyl$_3$—$C_1$–$C_8{}^+$, N-aryl$_2$—$C_5$–$C_6$-aryl-$C_5$–$C_6{}^+$, $C_1$–$C_6$-acyloxy, carboxylato of the formulae COOH and COOR$^{12}$, sulfinato, sulfonato of the formulae $SO_3H$ and $SO_3R^{12}$, phosphonato of the formulae $PO_3H_2$, $PO_3HR^{12}$ and $PO_3R^{12}{}_2$, where $R^{12}$ is either a monovalent cation, $NH_4{}^+$, $N(C_1$–$C_{10}$-alkyl)$_4{}^+$, $N(C_1$–$C_{10}$-alkyl/$C_6$–$C_{10}$-aryl)$_4{}^+$, $C_1$–$C_8$-alkyl or $C_6$-aryl, $C_1$–$C_6$-trialkylsilyl, NHCO-alkyl-($C_1$–$C_4$), COO-alkyl-($C_1$–$C_8$), CONH$_2$, CON(alkyl-($C_1$–$C_8$))$_2$, CO-alkyl-($C_1$–$C_8$), CO-alkenyl-($C_1$–$C_8$), NHCOO-alkyl-($C_1$–$C_4$), CO-aryl-($C_6$–$C_{10}$), CO-phenyl, COO-aryl-($C_6$–$C_{10}$), COO-phenyl, CHCH—CO$_2$-alkyl-($C_1$–$C_8$), CHCHCO$_2$H, and P is a trivalent phosphorus atom.

2. The process as claimed in claim 1, wherein bidentate ligands of the formula (IV) in which $R^6$ to $R^9$ are, independently of one another, $C_1$–$C_8$-alkyl, $C_5$–$C_6$-cycloalkyl, $C_6$-aryl, or are naphthyl, with these groups being able to be bear one or more substituents, preferably substituents selected independently from among hydrogen, $C_1$–$C_{10}$-alkyl, $C_1$–$C_6$-haloalkyl, $C_5$–$C_6$-cycloalkyl, $C_6$-aryl, phenyl, $C_1$–$C_6$-alkoxy, OCO-alkyl-($C_1$–$C_6$), O-aryl-$C_6$, $C_1$–$C_6$-trihalomethylalkyl, fluoro, chloro, bromo, iodo, nitro, hydroxy, oxo, thio, thiolato, amino, $C_1$–$C_8$-substituted amino of the types mono-, di-, tri-$C_1$–$C_8$-alkylamino or $C_2$–$C_8$-alkenylamino or mono- and di-$C_6$–$C_8$-arylamino or $C_1$–$C_8$-alkyl-$C_6$–$C_8$-arylamino, NH—CO-alkyl-$C_1$–$C_8$, NH—CO-aryl-$C_6$–$C_8$, $C_1$–$C_8$-acyloxy, carboxyl, carboxylato of the formula COOR$^{12}$, sulfinato, sulfonato of the formula $SO_3R^{12}$, phosphonato of the formula $PO_3H_2$, $PO_3HR^{12}$, $PO_3R^{12}{}_2$, where $R^{12}$ is either a monovalent or divalent cation ($Li^+$, $Na^+$, $K^+$, $Mg^{2+}$, $Ca^{2+}$), $NH_4{}^+$, $N(C^1$–$C_{10}$-alkyl)$_4{}^+$, $^{N(C}{}_1$–$C_{10}$-alkyl/$C_6$–$C_{10}$-aryl)$_4{}^+$, $C_1$–$C_6$-alkyl or $C_6$-aryl, and tri-$C_1$–$C_6$-alkylsilyl, are used.

3. The process as claimed in claim 1, wherein $R^6$ to $R^9$ are selected independently from the group consisting of ($C_3$–$C_8$)-alkyl, ($C_6$–$C_{10}$)-aryl, O—($C_5$–$C_8$)-alkyl, O—($C_6$–$C_0$)-aryl.

4. The process as claimed in claim 1, wherein $R^6$ and $R^7$ and/or $R^8$ and $R^9$ may be linked by a covalent bond so as to form a cyclic compound having from four to eight atoms.

5. The process as claimed in claim 1, wherein ligands in which $Y^1$ and $Y^2$ are each a direct phosphorus-carbon bond.

6. The process as claimed in claim 1, wherein Z comprises from one to four carbon atoms, in particular two carbon atoms.

7. The process as claimed in claim 1, wherein Z is a $C_1$–$C_6$-alkyl or $C_2$–$C_6$-alkenyl group or is part of a $C_3$–$C_8$-cycloalkyl, $C_5$–$C_8$-cycloalkenyl, $C_2$–$C_9$-heterocycloalkyl, $C_1$–$C_9$-heterocycloalkenyl, $C_6$–$C_{14}$-aryl, phenyl, naphthyl, fluorenyl or $C_2$–$C_{13}$-heteroaryl group, where the number of heteroatoms from the group consisting of can be 1–4 and all these groups may be monosubstituted or polysubstituted.

8. The process as claimed in claim 1, wherein ligands in which a three- to nine-membered ring system can be formed by Z, $X^1$, $X^2$, $P^1$ and $P^2$ together with a coordinated metal are used.

9. The process as claimed in claim 1, wherein 1,4-bis(diphenylphosphino)butane, 1,4-bis(dicyclohexylphosphino)-butane, 2-diphenylphosphinomethyl-4-diphenylphosphino-1-tert-butoxycarbonylpyrrolidine, 2,3-O-isopropylidene-2,3-dihydroxy-1,4-bis(diphenylphosphino)butane, (2R,3R,5R,6R)-2,3-dimethoxy-2,3-dimethyl-5,6-bis(diphenylphosphinomethyl)-1,4-dioxane, tris-(3-sulfophenyl)phosphine trisodium salt, 2,2'-bis[[bis(3-sulfophenyl)phosphino]methyl]-4,4',7,7'-tetrasulfo-1,1'-binaphthyl octasodium salt, diphosphinite ligands based on carbohydrates, 1,2-bis(diphenylphosphinoxy)ethane, (1R,2R)-(trans)-1,2-bis-(diphenyl-phosphinoxy)cyclohexane, (2R)-1-[[(diphenylphosphino)(cyclo-penthyl)amino]methyl]-2-diphenylphosphinoxy-3-(1-naphthalenyl-oxy)propane and/or (4S)-2-(2-(diphenylphosphino)phenyl)-4-isopropyl-1,3-oxazoline are used as ligands.

10. The process as claimed in claim 1, wherein the starting materials of the formulae (I) and/or (II) used are ones whose substituents $R^1$ to $R^4$ are each, independently of one another, hydrogen, ($C_1$–$C_{12}$)-alkyl, ($C_2$–$C_{12}$)-alkenyl, ($C_2$–$C_{12}$)-alkynyl, ($C_6$–$C_{10}$)-aryl, $CF_3$, COO-alkyl-($C_1$–$C_8$), $CONH_2$, CONHalkyl-($C_1$–$C_8$), CONalkyl$_2$-($C_1$–$C_8$), CO-alkyl-($C_1$–$C_8$), CO-phenyl, COO-phenyl, COO-aryl-($C_6$–$C_{10}$), CO-aryl-($C_6$–$C_{10}$), PO(aryl-$C_6$–$C_{10}$))$_2$, POalkyl$_2$—($C_1$–$C_4$), $PO_3H_2$, PO(alkyl-($C_1$–$C_4$))(O-alkyl-($C_1$–$C_4$)), PO(O-alkyl-($C_1$–$C_6$))$_2$ and Si(alkyl)$_3$-($C_1$–$C_8$), where alkyl is an unbranched or branched aliphatic or cyclic radical alkenyl is an olefinic hydrocarbon, alkynyl is an acetylenic hydrocarbon and aryl is an aromatic radical, and alkyl, alkenyl and alkynyl and also aryl may bear substituents selected independently from among hydrogen, O-alky-($C_1$–$C_8$), OCO-alkyl-($C_1$–$C_8$), O-phenyl, phenyl, aryl-$C_6$–$C_{10}$, fluorine, chlorine, bromine, iodine, OH, $NO_2$, Si-alkyl$_3$—($C_1$–$C_8$), $CF_3$, $SO_3H$, N-alkyl$_2$-($C_1$–$C_8$), $SO_2$-alkyl-($C_1$–$C_6$), SO-alkyl-($C_1$–$C_6$), NHCO-alkyl-($C_1$–$C_4$), COO-alkyl-($C_1$–$C_8$), $CONH_2$, CO-alkyl-($C_1$–$C_8$), CO-phenyl, COO-phenyl, COO-aryl-($C_6$–$C_{10}$), CO-aryl-($C_6$–$C_{10}$), PO-phenyl$_2$, POalkyl$_2$-($C_1$–$C_4$), $PO_3H_2$, POalkyl-$C_1$–$C_4$)(O-alkyl-($C_1$–$C_6$)), PO(O-alkyl-($C_1$–$C_6$))$_2$, and Si(alkyl)$_3$($C_1$–$C_8$), where alkyl and aryl are as defined above.

11. The process as claimed in claim 1, wherein the starting materials of the formulae (I) and/or (II) used are ones in which $R^1$ and $R^2$ and/or $R^3$ and $R^4$ are linked by covalent bonds so as to form a three- to nine-membered ring.

12. The process as claimed in claim 1, wherein metal complexes having central atoms selected from the group consisting of Rh, Ru, Ir, Pd, Pt, Ni, in particular ones containing rhodium as central atom, are used as homogeneous metal atom-ligand complex.

13. The process as claimed in claim 1, wherein alkyl is an unbranched or branched aliphatic or cyclic hydrocarbon and aryl is an aromatic radical.

14. The process as claimed in claim 13, wherein both alkyl and aryl bear substituents selected independently from among hydrogen, O-alkyl-($C_1$–$C_8$), O-phenyl, phenyl, aryl, fluorine, chlorine, OH, $NO_2$, Si-alkyl$_3$—($C_1$–$C_4$), $CF_3$, $SO_3H$, N-alkyl$_2$—($C_1$–$C_4$), CO-phenyl, COO-phenyl, COO-aryl-($C_6$–$C_{10}$), CO-aryl-($C_6$–$C_{10}$), PO-phenyl$_2$, POalkyl$_2$—($C_1$–$C_4$), PO(O-alkyl($C_1$–$C_6$))$_2$, and Si((alkyl)$_3$—$C_1$–$C_8$), where alkyl and aryl are as defined above.

15. The process as claimed in claim 1 where the catalyst system comprises one or more achiral or chiral bidentate ligands of the formula (IV)

$$(R^6Y^1)(R^7Y^1)P^1X^1ZX^2P^2(Y^2R^8)(Y^2R^9) \quad (IV).$$

16. The process as claimed in claim 1 in which further additives are used.

17. The process as claimed in claim 16 carried out using phosphine-rhodium complexes in the presence of acids.

18. The process as claimed in claim 1 carried out using phosphinite-rhodium catalysts without the addition of additives.

19. The process as claimed in claim 1, wherein the initial hydrogen pressure is from 0.1 to 300 bar.

20. The process as claimed in claim 1, wherein the catalyst system is used in an amount of from 0.001 to 5 mol %, based on the carbonyl component of the formula (I).

21. The process as claimed in claim 1, wherein solvents used are selected from the group consisting of alcohol, water, halogenated hydrocarbons, ethers, aromatic hydrocarbons, and mixtures thereof.

* * * * *